US005622698A

United States Patent [19]

Lee, Jr.

[11] Patent Number: 5,622,698

[45] Date of Patent: *Apr. 22, 1997

[54] METHOD AND COMPOSITION FOR INCREASING THE SUPERCOOLING POINT IN INVERTEBRATES

[75] Inventor: Richard E. Lee, Jr., Hamilton, Ohio

[73] Assignee: Miami University, Oxford, Ohio

[ * ] Notice: The terminal 29 months of this patent has been disclaimed.

[21] Appl. No.: 499,122

[22] Filed: Jul. 6, 1995

Related U.S. Application Data

[63] Continuation of Ser. No. 627,567, Dec. 10, 1990, abandoned, which is a continuation of Ser. No. 534,906, Jun. 8, 1990, abandoned.

[51] Int. Cl.$^6$ .............................. A01N 63/00; C12N 1/20

[52] U.S. Cl. .................. 424/93.4; 435/243; 435/252.34; 435/847; 435/874

[58] Field of Search .................................. 424/442, 93.1, 424/93.2, 93.3, 93.4; 514/2; 435/243, 252.34, 252.4, 252.3, 252.8, 172.3, 874, 847

[56] References Cited

U.S. PATENT DOCUMENTS 4,464,473 8/1984 Orser et al. .......................... 435/172.3

OTHER PUBLICATIONS

J. Strong–Gunderson, et al., Applied and Environmental Microbiology, vol. 58, No. 9, Sep. 1992, pp. 2711–2716.

R.E. Lee, et al., J. Insect Physiol., vol. 39, No. 1, pp. 1–12, 1993.

R.E. Lee, et al., J. Experimental Zoology 257:124–127 (1991).

Insects at Low Temperature, 1991, Eds. R.E. Lee and D.L. Denlinger, Chapman and Hall, New York and London.

R.E. Lee, et al., J. Economic Entomoology, vol. 87, No. 2, Apr. 1994, pp. 377–381.

R.E. Lee, et al., J. Economic Entomology, vol. 85, No. 2, Apr. 1992, pp. 371–374.

J. Strong–Gunderson, et al., J. Insect Physiol., vol. 37, No. 3, pp. 153–157, 1990.

Strong–Gunderson et al. 1989. Cryobiology 26(6):588.

*Primary Examiner*—Brian R. Stanton

*Attorney, Agent, or Firm*—Margaret A. Horn

[57] ABSTRACT

Ice nucleating agents are introduced into or on invertebrates. They elevate the supercooling point of such invertebrates. Where such invertebrates are freeze-intolerant, they may be killed or made susceptible to freezing by subjecting them to temperatures at or below the elevated supercooling point. Food sources treated with ice nucleating agents can be used to introduce the agents effectively to the invertebrate.

11 Claims, 3 Drawing Sheets

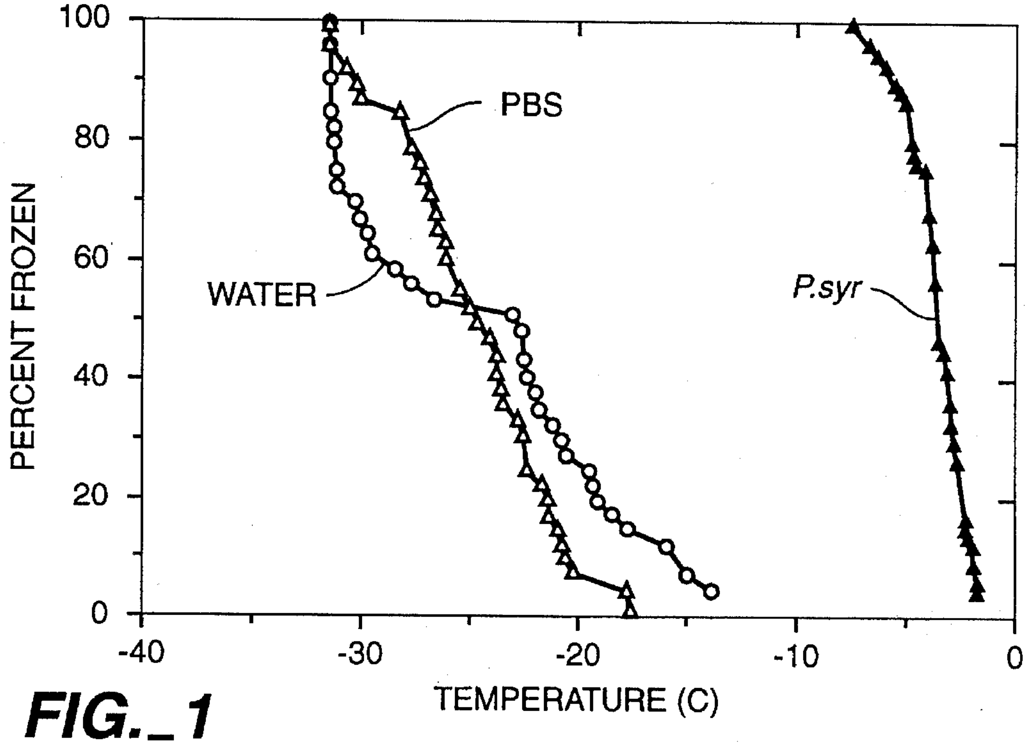
FIG._1
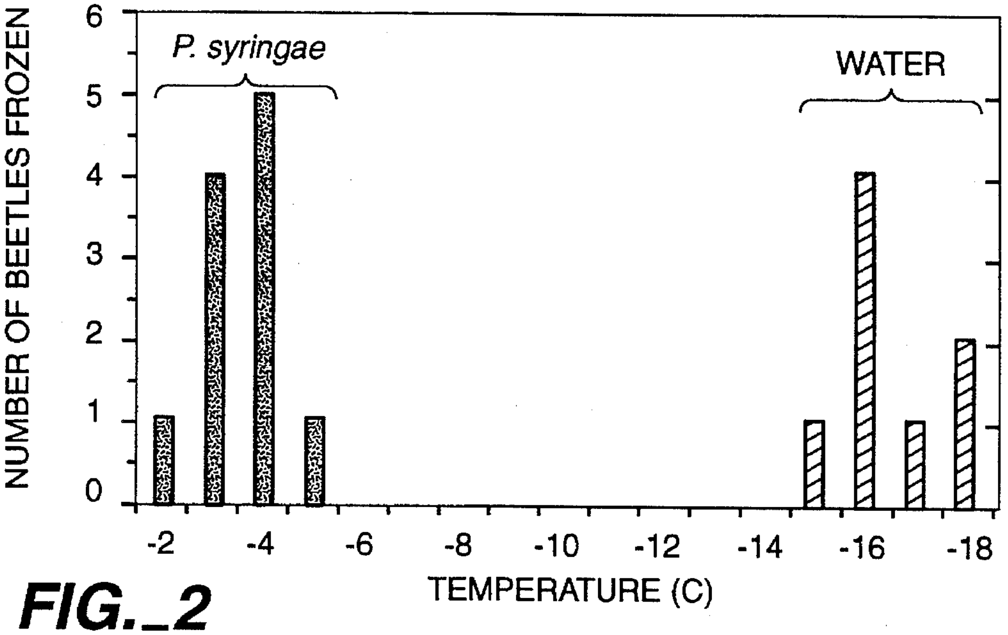
FIG._2

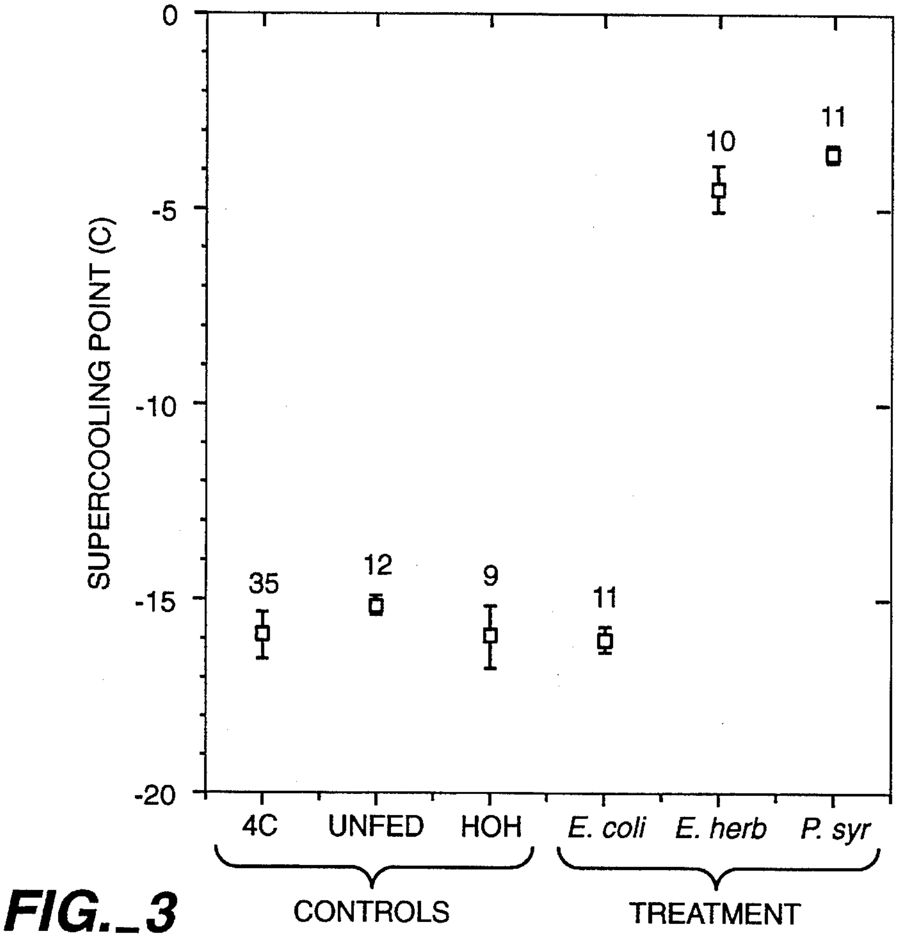
FIG._3
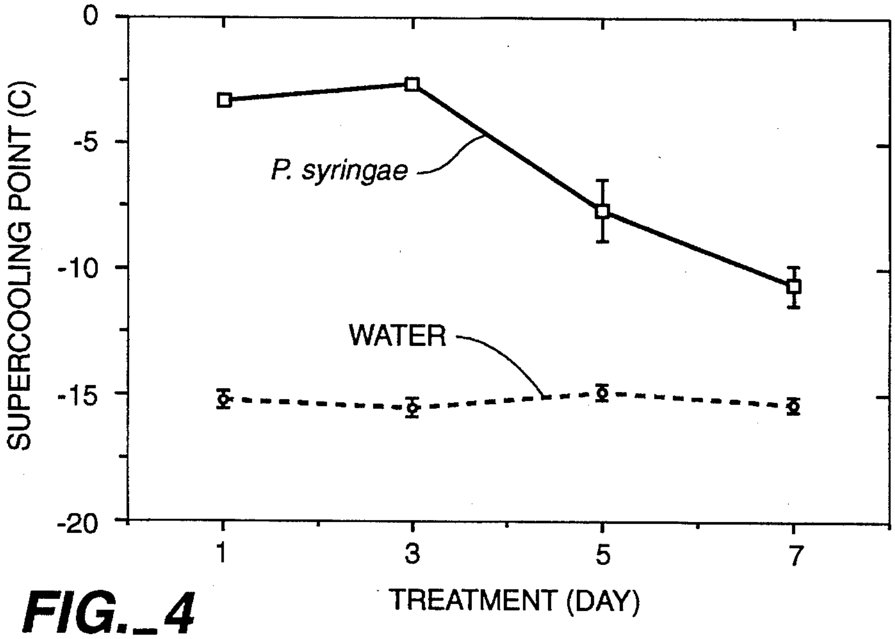
FIG._4

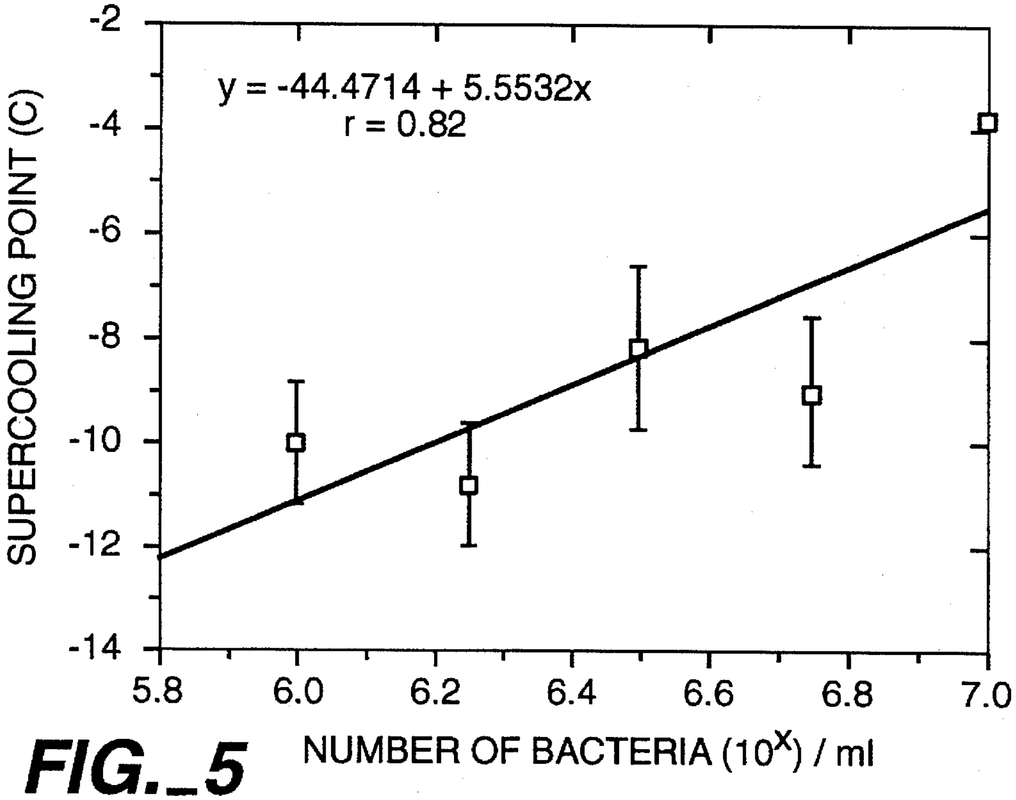
FIG._5

METHOD AND COMPOSITION FOR INCREASING THE SUPERCOOLING POINT IN INVERTEBRATES

This is continuation of application Ser. No. 07/627,567 filed Dec. 10, 1990, now abandoned, which is a continuation of application Ser. No. 07/534,906, filed Jun. 8, 1990, now abandoned.

FIELD OF THE INVENTION

The present invention relates to the ability to increase the supercooling point in invertebrates by applying an Ice Nucleating Agent (INA) to them. Particularly, such treatment can result in the killing of the invertebrate where it is freeze-intolerant and where the supercooling point is raised to at least an ambient temperature below 0° C. It has surprisingly been found that an effective way to deliver such INA is to apply them to the invertebrates food source.

BACKGROUND OF THE INVENTION

It is known that various agents and certain organisms are capable of initiating ice nucleation. Ice formation is currently of substantial commercial interest as a factor in inducing frost injury to plants, in atmospheric precipitation processes and in commercial snowmaking. Various organisms have been identified having an INA wherein the DNA sequences encoding for the INA (usually a protein) are provided or introduced into a host organism. See e.g. U.S. Pat. No. 4,464,473 incorporated herein by reference, which describes various bacteria having an INA. The INA can be separated from the host cell but often times the host cell can be used directly as a source of the agent. Although some overwintering invertebrates are able to survive internal ice formation, most can not. Many of these freeze-intolerant invertebrates increase their cold tolerance by synthesis of antifreeze proteins and/or the accumulation of large amounts of glycerol and other low-molecular weight polyols and sugars. The synthesis of such agents allow supercooling of the invertebrate by as much as 25° C. thus avoiding the injurious effects of such low temperatures, Baust et al (1985) Review—invertebrate Cold Hardiness: Facts & Fancy. J. invertebrate Physiol. 31:755–759. Of particular importance is the regulation of the temperature at which an invertebrate spontaneously freezes termed the supercooling point. As a freeze-intolerant invertebrate is cooled below 0° C. it does not freeze immediately, but supercooling several degrees before ice nucleation (formation) occurs. Increases in the supercooling capacity have been correlated with evacuation of the gut in some species; however the precise mechanism affecting supercooling invertebrates is unknown e.g. Somme (1982) Comp. Biochem. Physiol.,73A 519–543.

SUMMARY OF THE INVENTION

It has surprisingly been found that treatment of invertebrates with an INA increases the supercooling point of the invertebrate and under proper conditions can lead to an increase in the mortality rate.

Accordingly, the present invention relates to a method of increasing the supercooling point in an invertebrate comprising treating said invertebrate with an Ice Nucleating Agent. Further, the invention relates to a method of increasing the mortality rate or susceptibility to freezing in a population of freeze-intolerant invertebrates comprising:

a) treating the population with an INA sufficient to raise the supercooling point of the population; and b) subjecting the population to ambient temperatures below the raised supercooling point of the population.

The invention also relates to compositions useful for increasing the supercooling point in a desired invertebrate population comprising a food suitable for ingestion by or application of the invertebrate population to which has been applied an effective amount of an INA to raise the supercooling point of the population.

BRIEF DESCRIPTION OF THE DRAWINGS

FIG. 1 shows the cumulative freezing profile of forty, 10 μl—drops each of phosphate buffer, sterile distilled water and a suspension of $10^9$ bacteria/ml sterile distilled water of *Pseudomonas syringae*.

FIG. 2 shows the effect of ingesting ice nucleating active bacteria on the supercooling point of the adult lady beetle *Hippodamia convergens*.

FIG. 3 shows the effect of ingesting ice nucleating active bacteria on the supercooling point of adult lady beetles.

FIG. 4 shows the retention of ice nucleating active bacteria and its effects on the supercooling point of adult lady beetles.

FIG. 5 shows the effect of feeding lady beetles varying concentrations of *P. syringae* on the supercooling point.

DETAILED DESCRIPTION OF THE INVENTION

The term "invertebrate" as used herein refers to any of the numerous invertebrate animals such as Insects, Arthoropoda, Analids, Mollusks, Nematoda, Arachnida and Myriapoda. In a preferred embodiment such invertebrates are freeze-intolerant; that is, upon water crystallization due to freezing (the supercooling point) the organism is rendered inactive or is killed. Also preferred are invertebrates which are injurious to growing crops such as Indian meal moth (*Plodia interpunctella*), red flour beetle (*Tribolium castaneum*), flat grain beetle (*Cryptolestes Pusillus*), rusty grain beetle (*Cryptolestes ferrugineus*), shiny spider beetle (Gibbium Psylloides), lesser grain borer *Rhyzopertha dominica*), yellow mealworm (*Tenebrio molitor*), grainery weevil (*Sitophilus granarius*) and Southern corn rootworm and (*Diabrotica undecimtunctata howardi*) and the tarnish bug (*Lygus sp.*). Also preferred are any invertebrate which under the circumstances could be considered a pest.

An INA, as used herein, are agents which promote the formation of ice crystals within an aqueous media at a given temperature. Ice nucleating activity is described for compounds such as silver iodide, some amino acids, steroids and proteins and lipoproteins from invertebrate haemolymph. Of particular importance, and a preferred embodiment of this invention are those INAs found in cells such as microbial cells notably bacteria. They are presently unique in their ability to induce nucleation at 1°–2° below 0° C. In these microbial cells are contained DNA which encodes for a protein having ice nucleating activity. Cells can be used as whole cells or the INA can be separated out of such cells. Cells can also be lysed or otherwise produce pieces of cellular material (e.g. membranes) in which such INA's are found or trapped. Such ice nucleation active bacteria preparations are available commercially, for example, dry powdered *Pseudomonas syringae* available from Genencor International, Rochester, N.Y. Where the INA is in a microbial cell the DNA may be introduced into a second recipient host such that the heterologous DNA sequence encodes an INA. Such DNA segments may be introduced by a plasmid, virus or other self replicating element or non-replicating vectors targeting for integration into a host organism. The host may then be grown and cloned and clones having ice nucleating activity isolated. An effective amount of INA refers to the amount applied, ingested, etc. by the invertebrate sufficient to cause a change in the supercooling point of the invertebrate.

An invertebrate can be treated with an INA according to the invention in a number of ways. For example, a solution or suspension of an INA may be topically applied to the invertebrate on either the dorsal or ventral surface or both to initiate freezing transcuticularly of the invertebrate. Another method may be to subject the invertebrate to a coated surface such that the invertebrate walking or crawling across the surface will accumulate sufficient INA to elevate the supercooling point. In another aspect of the invention, the invertebrate may be caused to ingest the INA by ingesting a solution or suspension of an INA or in a preferred embodiment by oral ingestion of a food source of the invertebrate which has the INA applied to it. An example of the preferred embodiment would be to treat a grain such as corn or wheat with an INA wherein the grain is susceptible to being eaten or otherwise destroyed by a pest. Any such unwanted pest ingesting the grain and a corresponding sufficient amount of INA would then be susceptible to freezing and an elevated supercooling point. The exact concentration of INA will vary from INA to INA, the delivery route and external environmental conditions and will be within the skill in the art to choose such sufficient concentrations. For example, a sufficient amount applied to a grain would be calculated based on the amount of grain expected to be eaten by or applied to the surface of the invertebrate resulting in a final concentration sufficient to elevate the supercooling point to the desired level. The time that an INA will effect an increase in supercooling point in an invertebrate will vary. Where the INA is topically applied, the INA is subject to removal by abrasion, rain, wind, etc. and may only last a short period of time. Where the INA is ingested, the INA effect may last seven days or more. Where the INA is in bacteria, it is possible the bacteria will survive in the gut and will remain active so long as the bacteria remains. When selecting an INA one skilled in the art will be able to choose appropriate agents for use. In general, the agent chosen should be one that effects a supercooling point above the natural supercooling point of the organism. So, for example, *P. syringae* having an INA could be selected; which increases the natural supercooling point of distilled water from (−13° C.) to about −1.6° C. The convergent lady beetle, *H. convergens* has a supercooling point of about −15° C. The *P. syringae* INA could be chosen to elevate the supercooling point above the −15° C. with the proper concentrations. Wherein, when applied, the supercooling point is elevated to about −3.5° C.

In order then to affect the mortality rate of a population, the population must be of a freeze-intolerant invertebrate having a supercooling point below that of the INA selected. Once the invertebrate population has been treated, the population will need to be subjected to ambient temperatures below the new supercooling point to increase mortality or susceptibility to freezing. This can be accomplished by subjecting the treated population to ambient temperatures such as would naturally occur during natural outdoor temperatures or by lowering the temperature of the population by localized artificial temperature control. The following experimental data is not intended to be limiting. It is designed to show that INAs can successfully be used to increase the supercooling point of an invertebrate. One skilled in the art could substitute appropriate invertebrates, INAs, conditions, etc. as necessary within the scope of the invention.

EXAMPLES

I. INGESTION OF ICE NUCLEATING BACTERIA INCREASES SUPERCOOLING POINT OF *H. CONVERGENS*

Rearing

Bacterial strains of *P. syringae* provided by S. E. Lindow (University of California, Berkeley), *E. herbicola* provided by L. R. Maki (The University of Wyoming) (strain 265G-2) and *Escherichia coli* K12 derived from strain AB301 provided by J. R. Johnson (Miami University, Oxford, Ohio) were identified and confirmed by their biochemical reactions utilizing the API 20E system (Analytab Products, Plainview, N.Y. 11803). Bacteria were maintained at 20°±0.1° C. on Bacto nutrient agar (Difco) plates with 2.5% glycerol added to enhance ice-nucleating activity, plates were incubated at 20° C. for 7 days prior to preparation of bacterial suspensions utilized in subsequent feeding trials. Adult *H. convergens* were collected from overwintering aggregations in California, and held unfed at 4° C. until used for experimentation.

Supercooling point determination

Supercooling point values were determined by positioning beetles in contact with a 30-gauge copper-constantan thermocouple within a 1.5 ml polypropylene tube. These tubes were placed into glass test tubes suspended in a 0° C. refrigerated bath and allowed to equilibrate for 5 min before cooling at approx. 0.3° C./min. The lowest temperature reached prior to the release of the latent heat of crystallization was recorded as the supercooling point.

Bacterial suspension and lady beetle treatment

In determining the number of bacteria/ml of solution, suspensions of 0.5 absorbance, at 660 nm (Baush and Lomb Spectronic 20) were made in sterile distilled water for each strain. Bacterial counts were determined utilizing a custom-made haemocytometer with a reduced cell depth of 0.02 Mm and improved double Neubauer ruling (Hausser Scientific Co.). Aqueous serial dilutions of each bacterial species to be used in ice-nucleating active assays and feeding experiments were made from $10^9$ to $10^5$ bacteria/ml sterile water based upon initial total bacterial counts.

Approximately 50 adult lady beetles were placed in a 150×15 mm Petri dish and fed the bacterial suspensions using 200μl capillary tubes plugged at one end with cotton and filled with sterile water or one of the 3 aqueous bacterial suspensions (*P. syringae, E. herbicola* or *E. coli*). Five capillary tubes were placed in each Petri dish containing the beetles and transferred to a 20° C. incubator. Each treatment group was fed for 48 h on the bacterial suspension prior to supercooling point determination. Beetles were monitored initially to be certain they were drinking from the tubes. Fresh bacterial suspensions were made daily.

Effect of ice-nucleating active bacterial concentrations on the supercooling point Twenty beetles were placed in Petri dishes containing varying suspensions, $10^9$, $10^8$, $10^7$, $10^{6.75}$, $10^{6.25}$ or $10^5$ of *P. syringae*/ml sterile water. Suercooling points (N=12) were determined after 48 h of feeding. Fresh bacterial suspensions were made daily.

Recovery of ice-nucleating active bacteria from the invertebrate gut.

Lady beetles fed ice-nucleating active bacteria for 48 h were dissected under aseptic conditions. Gut content was plated onto nutrient agar containing 2.5% glycrol and 0.5% cycloheximide. The plates were incubated 7 days at 20° C. and a suspension in phosphate-buffer saline was made of each morphologically distinct colony (absorbance 0.5% approx. $10^9$ bacteria/ml sterile phophate-buffer saline). From this suspension ten 10 μl—drops were placed on an aluminum boat, floating on a refrigerated alcohol bath. A surface temperature −6.5° ±0.3° C., was maintained. The droplets were observed for 1–5 min for freezing; initially droplets appear "clear" and turn opaque after freezing occurs. Questionably frozen droplets were touched with a sterile probe; if freezing occurred as a consequence of probing, these data were not included with droplets that froze spontaneously.

Retention of ice-nucleating active bacteria following ingestion

Approximately 50 beetles were placed in a Petri dish and fed *P. syringae* ($10^9$ bacteria/ml sterile water). A fresh bacterial suspension of *P. syringae* was made daily. After 48 h of feeding the suspension was replaced with sterile distilled water and supercooling points checked at 1, 3, 5 and 7 days post *P. syringae* treatment. Fresh water was added daily.

Effect of ice-nucleating active bacteria on the supercooling capacity of water and phosphate buffer The freezing profile of sterile distilled water, phosphate-buffer solution and *P. syringae* ($10^9$ bacteria/ml sterile phosphate-buffer solution) is shown in FIG. 1. All three treatments were run concurrently, on individual boats, with twenty 10 μl—droplets (a total of 40 droplets/solution) placed on each boat floating on a refrigerated bath. Both phosphate-buffer solution and sterile water supercooled extensively and began freezing only after temperatures of −17° and −13° C. respectively were reached. This result contrasts sharply with the freezing profile of *P. syringae* containing solutions where droplets began freezing at −1.6° C. with 100% of the samples frozen by −7.4° C. Thus, the addition of *P. syringae* to phosphate-buffer saline greatly reduced its supercooling capacity. Since this saline proved lethal to the invertebrates, all subsequent bacterial suspensions were made with sterile water.

Effect of ice-nucleating active bacteria on the supercooling point of beetles

Unfed adult beetles normally supercool to −16.0°±0.6° C. when tested immediately after removal from 4° C. (FIG. 2 and 3). Beetles fed a suspension of *P. syringae* ($10^9$ bacteria/ml sterile water) showed a dramatic elevation in the mean supercooling point to −3.5°±0.2° C., an increase of 12.5° C. A second type of ice-nucleating active bacteria, *E. herbicola*, was fed to the beetles for 48 h ($10^9$ bacteria/ml sterile water), and resulted in a significant supercooling point elevation, −4.4°±0.6° C. (FIG. 3). Controls include: beetles fed only distilled water or unfed and held at 20° C. for 48 h, supercooling points for all individuals in both groups were below −15° C., and beetles fed a non-ice-nucleating active bacteria, *E. coli* at $10^9$ bacteria/ml sterile water, mean supercooling point, −16.0°±0.4° C. indicating, as expected, a lack of ice-nucleating activity in this control species (FIG. 3).

Retention of ice-nucleating active bacteria in the intestinal tract of *H. convergens*

Lady beetles were fed a suspension of *P. syringae* ($10^9$ bacteria/ml sterile water) for 48 h when the feeding tubes were replaced with ones containing sterile distilled water. Supercooling points of the beetles were tested at 1,3,5 and 7 days after the *P. syringae* suspension was removed (FIG. 4). Mean supercooling points for beetles 1 and 2 days after treatment were −3.5° and −2.8° C. respectively, a substantial elevation in supercooling point values with little variation among individual values within the treatment groups. A decrease in the supercooling point was observed on days 5 and 7 which coincided with an increase in the variability of the supercooling point values. At 5 days after treatment 6 of 12 individual supercooling point values were between −3.6° and −4.6° C. with the remainder between −10.1° and −14.8° C. Even after 7 days, beetles maintained supercooling points that were slightly higher than control beetles fed only distilled water. Mean supercooling point values at 1,3 and 5 days after treatment were significantly greater than control means (F=28.39, P.=0.001). Further more, it was possible to recover *P. syringae* from the gut of beetles after being fed this bacterium.

Effects of various bacterial concentrations on the supercooling point

Various concentrations of *P. syringae* were fed to beetles for 48 h (FIG. 5). Serial dilutions of *P. syringae* between $10^6$ and $10^{6.75}$ bacteria/ml sterile water slightly elevated the mean supercooling points to approx. −9.5° C. A suspension of $10^7$ was the lowest concentration of *P. syringae* that showed a marked elevation in the supercooling −3.9°±0.1° C. (FIG. 5). Supercooling points were positively correlated (r=0.82) with increasing concentrations of the ice-nucleating active bacteria.

II. TRANSCUTICULAR EFFECT

Two ice nucleating active (INA) bacteria *Pseudomonas syringae* and *erwinia herbicola* are epiphytic plant pathogens. In the absence of INA bacteria many plants supercool to −8° C. or below before their tissues spontaneously freeze. These bacteria initiate freezing on the leaf, across the plant cuticle. We investigated whether these bacteria have the capability to nucleate across the invertebrate cuticle. The lady beetle, *H. convergens*, was chosen. Topical application of a suspension of *P. syringae* ($10^9$ bacteria/ml water) to the ventralsurface of the beetle significantly elevated the SCP to −4.4° C. compared to that of sterile water, −6.4° C. ($P<0.05$). The application of suspensions of *P. syringae* to the cuticle of a variety of invertebrates caused an elevation of the SCP. In a second experiment we determined that if a solution of *P. syingae* was applied to the ventral surface of beetles and allowed to dry, an increase in the SCP was still apparent.

Effect of INA Bacteria on the Supercooling Capacity of invertebrates:

The southern corn rootworm and tarnish bug are freeze susceptible invertebrates that die when ice forms within their bodies. The misting of a solution of *P. syringae* onto their surface caused a significant increase in the temperature at which ice spontaneously formed within their tissues (Table 1). For the southern corn rootworm the mean supercooling point value increased from −7.5° C. in individuals misted with water to −3.2° C. for invertebrates treated with a solution of *P. syringae*. The loss of supercooling capacity was even more dramatic in the tarnish bug where supercooling points values increased by 11.3° C.

III. STORED GRAIN COMPOSITIONS

In the following examples where a dry powdered form of *P. syringae* was used, the product was commercially available from Genencor International Rochester, N.Y.

List of invertebrate pests of stored grain examples:

Indian meal moth (*Plodia Interpunctella*)
Red flour beetle (*Tribolium castaneum*)
Flat grain beetle (*Cryptolestes pusillus*)
Rusty grain beetle (*Cryptolestes ferrugineus*)
Shiny spider beetle (*Gibbium psylloides*)
Lesser grain borer (*Rhyzopertha dominica*)
Yellow mealworm (*Tenebrio molitor*)

Grainery weevil (*Sitophilus granarius*)

Effect of INA Bacteria on Low Temperature Survival of Stored Grain invertebrates Pests: These experiments were designed to simulate the conditions that stored grain invertebrate pests would experience in a grain bin. Ten grams of wheat or corn that had been inoculated with invertebrates was treated with dry, powdered *P. syringae* and held at 23° C. for 24 hours. Treatment doses were based on the weight of dry, powdered *P. syringae* to weight of grain. The samples were next transferred directly to −5° or −8° C. for 24 hours in a refrigerated bath. Following a final 24 hours at 23° C. the proportion of surviving invertebrates was determined.

Effect of INA Bacteria on Low Temperature Survival of Stored Grain invertebrate Pests:

Of the untreated control invertebrates exposed to −5° C. for 24 hours in wheat, six species exhibited survival rates between 90–98% (Table 2). However, two species had significant levels of mortality; only 43% of the *C. pusillus* adults and 19% of *T. castaneum* adults survived. At −8° C. the control groups of three species exhibited survival rates of 77% or higher. No individuals of *C. pusillus, T. castaneum* or *R. dominica* survived 24 hours of exposure to −8° C.

The application of 100 or 1000 ppm of dry powdered *P. syringae* resulted in a statistically significant decrease in survival for all 8 species tested at −5° C. in wheat (Table 2). For two species, *C. ferrugineus* and *R. dominica*, the application of 100 ppm reduced survival, from 90% or higher in the control, to less than 5%. In five species no individual survived exposure to −8° C. after treatment with 1000 ppm of *P. syringae*. In the grainery weevil survival decreased to 48% versus 96% survival in the control group. Larvae of *T. molitor* were the most resistant species to treatment with 1000 ppm.

At −8° C. for the five species in which 50% or more of the individuals in the control group survived, all exhibited a statistically significant decrease in their rate of survival following treatment with 100, 1000 ppm or both treatments of dry powdered *P. syringae*. Furthermore, in four of these five species, *S. granarius, C. ferrugineus, P. interpunctella* and *G. psylloides*, treatment with 1000 ppm of *P. syringae* reduced survival rates to 4% or less following exposure to −8° C.

In another experiment corn was substituted for wheat and the effect of *P. syringae* on low temperature was tested (Table 3). Treatment with 100 ppm *P. syringae* caused a statistically significant decrease in survival following exposure to −8° C.; in the rusty grain beetle all adults died following this treatment. In the grainery weevil all adults were killed after exposure to 1000 ppm.

TABLE 1

Effect of misting insects with a suspension of *Pseudomonas syringae* on their supercooling points. Mean ± SEM, n = sample size.

| Species | Supercooling Point (°C.) Control[1] | *Pseudomonas syringae*[2] |
|---|---|---|
| *Diabrotica undecimpunctata* howardl (Southern corn rootworm) | −7.5 ± 0.8 (n = 11) | −3.2 ± 0.2* (n = 10) |
| Lygus sp. (Tarnish bug) | −20.0 ± 0.5 (n = 25) | −8.7 ± 1.0* (n = 17) |

*significant at $P < 0.01$, Student's T-test
[1]Control ≡ Insects misted with water
[2]Solution of ~ $10^9$ cells/ml of *Pseudomonas syringae* strain

TABLE 2

The effect of exposure to ice nucleating active bacteria on survival of larval and adult stored grain insect pests in wheat exposed to subzero temperatures. Insects were treated with dry powdered *Pseudomonas syringae* (Snomax ™) for 24 hours at 23° C. prior to 24 hours exposure to −5 or −8° C. Survival was assessed after a 24-hour recovery period at 23° C. Numbers in parentheses indicate the number of survivors/total number of insects tested.

| | SURVIVAL FOLLOWING EXPOSURE TO LOW TEMPERATURE | | | | | |
|---|---|---|---|---|---|---|
| | Exposed to −5° C. for 24 hr | | | Exposed to −8° C. for 24 hr | | |
| | Untreated | *Pseudomonas syringae* | | Untreated | *Pseudomonas syringae* | |
| | Control | 100 ppm | 1000 ppm | Control | 100 ppm | 1000 ppm |
| *Tenebrio molitor* (yellow mealworm larvae) | 97% (29/30) | 77% (23/30)* | 73% (22/30)* | 77% (23/30) | 23% (7/30)** | 53% (16/30) |
| *Sitophilus granarius* (grainery weevil adults) | 96% (27/28) | 62% (18/29)* | 48% (15/31)** | 84% (27/32) | 23% (7/31)** | 3.6% (1/28)** |
| *Cryptolestes ferrugineus* (rusty grain beetle adults) | 97% (28/29) | 0% (0/30)** | 0% (0/25)** | 90% (28/31) | 0% (0/29)** | 0% (0/25)** |
| *Piodie interpunctella* (Indianmeal moth larvae) | 98% (23/24) | 36% (10/28)** | 3.8% (1/26)** | 67% (20/30) | 0% (0/27)** | 0% (0/30)** |
| *Cryptolestes pusillus* (flat grain beetle adults) | 43% (13/30) | 0% (0/29)** | 0% (0/20)** | 0% (0/48) | 0% (0/30) | 0% (0/29) |
| *Tribolium castaneum* (red flour beetle adults) | 19% (6/31) | 0% (0/29)* | 0% (0/30)* | 0% (0/31) | 0% (0/31) | 0% (0/30) |
| *Rhyzopertha dominica* (lesser grain borer adults) | 90% (27/30) | 3.6% (1/28)** | 0% (0/31)** | 0% (0/31) | 0% (0/30) | 0% (0/30) |
| *Gibbium psylloides* (shiny spider beetle adults) | 93% (28/30) | 25% (8/32)** | 0% (0/30)** | 53% (16/30) | 0% (0/30)** | 0% (0/31)** |

*Significant at $P < 0.05$
**Significant at $P < 0.001$

TABLE 3

The effect of exposure to ice nucleating active bacteria on survival of larval and adult stored grain insect pests in corn exposed to subzero temperatures. Insects were treated with dry powdered *Pseudomonas syringae* for 24 hours at 23° C. prior to 24 hours exposure to −5 or −8° C. Survival was assessed after a 24-hour recovery period at 23° C. Numbers in parenthesis indicate the number of survivors/total number of insects tested.

| | SURVIVAL FOLLOWING EXPOSURE TO −8° C. FOR 24 HR | | |
|---|---|---|---|
| | Untreated | *Pseudomonas syringae* | |
| | Control | 100 ppm | 1000 ppm |
| *Sitophilus granarius* (grainery weevil adults) | 73% (22/30) | 23% (7/30)** | 0% (0/30)** |
| *Cryptolestes ferrugineus* (rusty grain beetle adults) | 83% (25/30) | 0% (0/30)** | 0% (0/30)** |

**Significant at $P < 0.001$

What is claimed is:

1. A method of increasing the supercooling point in an insect thereby increasing its susceptibility to freezing at temperatures above its natural supercooling point, comprising:

treating said insect with an amount of an ice nucleating agent sufficient to increase the supercooling point of the insect above the natural supercooling point of the insect;

wherein said ice nucleating agent is a bacterium selected from the group consisting of *Pseudomonas syringae* and *Erwinia herbicola.*

2. A method according to claim 1 wherein the ice nucleating agent is orally ingested by the insect.

3. A method according to claim 2 wherein said ice nucleating agent is applied to a food source for the insect.

4. A method according to claim 1 wherein the insect is freeze-intolerant.

5. A method according to claim 1 wherein said ice nucleating agent is applied topically to one or more surface(s) of the insect.

6. A method of killing individual insects in a population of freeze-intolerant insects comprising:

a) treating the population of insects with an amount of ice nucleating agent sufficient to raise the supercooling point of the population above the natural supercooling point of the population of insects; and b) subjecting the population of insects to temperatures at or below the raised supercooling point of the population;

wherein said ice nucleating agent is a bacterium selected from the group consisting of *Pseudomonas syringae* and *Erwinia herbicola.*

7. A method according to claim 6 wherein the population of insects is treated by causing the ice nucleating agent to be orally ingested by the insects.

8. A method according to claim 7 wherein the ice nucleating agent is applied to a food source for the population of insects.

9. A method according to claim 6 wherein the ice nucleating agent is topically applied to one or more surface(s) of an the insects.

10. A method according to claim 6 wherein the population is treated with between about 100 to 1000 parts per million of *Pseudornonas syringae* bacterium per 10 grams of stored grain or wheat.

11. A method according to either of claims 1 or 6 wherein the insect is selected from the group consisting of lady beetle (*Hippodamia convergens*), Indian meal moth (*Plodia interpunctella*), red flour beetle (*Tribolium castaneum*), flat grain beetle (*Cryptolestes pusillus*), rusty grain beetle (*Cryptolestes ferrugineus*), shiny spider beetle (*Gibbium psylloides*), lesser grain borer (*Rhyzopertha dominica*), yellow mealworm (*Tenebrio molitor*), grainery weevil (*Sitophilus granarius*), southern corn rootworm (*Diabrotica undecimtunctata howardi*) and tarnish bug (*Lygus sp.*).

* * * * *